United States Patent

Sumner, Jr. et al.

[11] Patent Number: 5,840,970
[45] Date of Patent: Nov. 24, 1998

[54] PROCESS FOR THE PURIFICATION OF NAPHTHALENEDICARBOXYLIC ACID

[75] Inventors: Charles Edwan Sumner, Jr.; Arthur Thaler Spaugh, Jr., both of Kingsport, Tenn.

[73] Assignee: Eastman Chemical Company, Kingsport, Tenn.

Related U.S. Application Data

[60] Provisional application No. 60/060,889, Oct. 3, 1997.

[21] Appl. No.: 100,367

[22] Filed: Jun. 19, 1998

[51] Int. Cl.$^6$ .................................................... C07C 51/23

[52] U.S. Cl. ............................................................ 562/487

[58] Field of Search ..................................... 562/487, 416, 562/417

[56] References Cited

U.S. PATENT DOCUMENTS

| | | |
|---|---|---|
| 3,888,921 | 6/1975 | Yamamoto et al. . |
| 4,933,491 | 6/1990 | Albertins et al. . |
| 5,183,933 | 2/1993 | Harper et al. . |
| 5,254,719 | 10/1993 | Holzhauer et al. . |
| 5,292,934 | 3/1994 | Sikkenga et al. . |

*Primary Examiner*—Samuel Barts
*Attorney, Agent, or Firm*—Andrew B. Griffis; Harry J. Gwinnell

[57] ABSTRACT

Disclosed is a process for the purification of a naphthalenedicarboxylic acid (NDA) which has been manufactured by the oxidation of a dialkylnaphthalene in the presence of a molecular oxygen-containing gas and a heavy metal-containing catalyst and contains metal residues, e.g., cobalt and manganese residues, as impurities. The process involves contacting an acetic acid slurry of a NDA, typically 2,6-naphthalenedicarboxylic acid, containing such metals, with acetic anhydride.

4 Claims, No Drawings

5,840,970

PROCESS FOR THE PURIFICATION OF NAPHTHALENEDICARBOXYLIC ACID

REFERENCE TO RELATED APPLICATION

This application claims the benefit of U.S. Provisional application Ser. No. 60/060,889 filed Oct. 03, 1997.

SUMMARY OF THE INVENTION

This invention pertains to the purification of a naphthalenedicarboxylic acid (NDA) which has been manufactured by the oxidation of a dialkylnaphthalene in the presence of a molecular oxygen-containing gas and a heavy metal-containing catalyst. More specifically, this invention pertains to the removal of heavy metal impurities such as cobalt and manganese present in a NDA, typically 2,6-naphthalenedicarboxylic acid (2,6-NDA), prepared by the heavy metal-catalyzed oxidation of a dialkylnaphthalene, typically 2,6-dimethylnaphthalene (2,6-DMN), by contacting a mixture of an NDA in a finely divided form in acetic acid with acetic anhydride.

BACKGROUND OF THE INVENTION

NDA is employed as a monomer in the production of high performance polyesters such as poly(ethylene 2,6-naphthalenedicarboxylate) (PEN) and liquid crystal polyesters. PEN has superior gas barrier properties to relative to poly(ethylene terephthalate) (PET) and also can be used for the fabrication of hot-fill plastic containers. NDA typically is prepared by the liquid-phase catalyzed autoxidation of a dialkylnaphthalene, especially 2,6-DMN. The crude NDA oxidation product contains many impurities which precludes its use directly in the synthesis of polymers. Such impurities may adversely affect the performance and color of polymers prepared therefrom and can interfere with the polymerization process used in the synthesis of the polymer. These impurities typically include the catalyst metals themselves in addition to organic impurities formed during the oxidation. Timellitic acid (TMA) which is produced as a by-product during the liquid-phase oxidation of DMN to NDA forms an insoluble complex with heavy metals such as cobalt and manganese used in the oxidation catalyst system. The TMA/heavy metal complexes are insoluble in the acetic acid/water used as the solvent/reaction medium for the oxidation process and, therefore, precipitate from the reaction mixture and are removed as solids with the solid NDA product. The precipitation of the heavy metal, catalyst metals also can cause deactivation of the oxidation catalyst resulting in a partial or complete shut-down of the oxidation process.

The removal of impurities from NDA is very difficult due to the high melting point of NDA (>300° C.) and it has very low solubility in most conventional organic solvents used in commercial processes. Conversion of NDA to its dimethyl ester, e.g., 2,6-dimethylnaphthalenedicarboxylate (NDC) may represent the best method for purification. However, the formation of the dimethyl ester alone does not give a sufficiently pure ester monomer requiring further purification of the NDC. U.S. Pat. No. 5,254,719 discloses a process for the purification of NDA by reaction with methanol in the presence of sulfuric acid. The sulfuric acid is necessary to solubilize the catalyst metals present in the NDA and allow their removal with the mother liquor. The resulting NDC is recrystallized and distilled. If the catalyst metals are not removed from the NDC purification stream, they can cause the distillation column to plug and cause fouling of a purge stream. Furthermore, it is important to recover for reuse the catalyst metals due to their expense.

Other methods of removal of catalyst metals are disclosed in U.S. Pat. No. 5,183,933 which describes a process comprising adding water to the oxidizer effluent in a quantity sufficient to achieve a 30 weight percent aqueous solution (70% acetic acid). The relatively high water concentration causes the catalyst metals to remain soluble and allow their separation from the NDA. However, the resulting mother liquor contains too much water to be directly recycled to the oxidation process contemplated by U.S. Pat. No. 5,183,933, requiring the removal of some of the water present. A second method disclosed by this patent involves the addition of oxalic acid to the mother liquor obtained after removal of the crude NDA and heating the resulting oxalic acid solution at 260° C. to precipitate the metal oxalate complexes. This method does not provide for the removal of the catalyst metals from the crude NDA.

U.S. Pat. No. 5,292,934 discloses a purification process wherein the oxidizer effluent is subjected to a high temperature treatment to convert the TMA into a mixture of terephthalic and isophthalic acids, thereby liberating and solubilizing the catalyst metals and permitting their recycle to the oxidation mixture. This method requires specialized heating techniques to achieve the high temperatures (315° C.) required for the decomposition of the TMA. U.S. Pat. No. 4,933,491 discloses the reaction of NDA with a substantial excess of acetic anhydride to convert the NDA to a mixed NDA-acetic acid anhydride to provide a soluble product which can be purified by recrystallization. Subsequent hydrolysis of the purified mixed NDA-acetic acid anhydride gives NDA having improved purity. The amount of acetic anhydride utilized in the process of U.S. Pat. No. 4,933,491 ranges from 5 to 100 moles anhydride per mole of crude NDA. U.S. Pat. No. 3,888,921 discloses a process wherein crude NDA is dissolved in aqueous alkali and precipitated as the monosodium salt at a pH of 6.3–6.8. Strict control of the pH is required to avoid precipitation of isomers of NDA and other impurities.

DESCRIPTION OF THE INVENTION

We have found that heavy catalyst metals such as Co and Mn can be removed from crude NDA by treating the crude NDA with relatively small amounts of acetic anhydride. Thus, the process of the present invention provides for the removal of, i.e., a reduction in the concentration of, impurities comprising heavy metal catalyst residues and TMA from NDA, preferably 2,6-NDA, by contacting a mixture comprising a slurry of finely divided NDA, containing such impurities, in acetic acid with acetic anhydride, wherein the metal impurities are present as complexes with trimellitic acid and the amount of acetic anhydride employed gives an acetic anhydride:TMA mole ratio of about 1:1 to 5:1. The acetic anhydride is believed to react with the insoluble TMA/Co complex and/or TMA/Mn complex to produce trimellitic anhydride and the Co and/or Mn acetates which are soluble in the acetic acid solvent. This allows the crude NDA to be partitioned from the catalyst metals and resulting trimellitic anhydride by filtration. It is possible, of course, that the crude NDA contains some heavy catalyst metals (Co and Mn) which are not in complex association with TMA.

The process of the present invention may be carried out by first separating a crude NDA from an oxidation mother liquor and then preparing a slurry of the solid NDA containing insoluble TMA/Co complex and/or TMA/Mn complex in acetic acid. The acetic acid purification medium initially may contain the appropriate amount of acetic anhydride or alternatively some or all of the acetic anhydride may be added to the NDA/acetic acid slurry after is formation.

The amount of acetic acid employed may vary considerably depending on various factors such as the particular apparatus employed in the purification and the oxidation process operated in conjunction with the purification process in which the acetic acid solution of the catalyst metals is used. For practical reasons, the acetic acid:NDA weight ratio normally is in the range of about 1:1 to 10:1, preferably about 1:1 to 3:1 and most preferably about 1:1 to 1.5:1. The amount of acetic anhydride required to achieve a significant reduction in the amount of heavy metals present in the crude NDA depends upon the amounts of metals and TMA present in the crude NDA. Typically, the mole ratio of acetic anhydride:TMA should be at least 1:1 and preferably is in the range of about 1:1 to 5:1. These acetic anhydride:TMA mole ratios are based on anhydrous TMA. Any water present in the crude NDA and/or associated with the TMA/Co and TMA/Mn complexes will react with acetic anhydride, thereby requiring additional acetic anhydride to achieve an acetic anhydride:TMA mole ratio of about 1:1 to 5:1. The crude NDA produced in the oxidation of DMN can be analyzed periodically for TMA and then the amount of acetic anhydride used in the purification process can be adjusted accordingly.

The amount of acetic anhydride employed in the process of the present invention is substantially less than the amount that is used in the process of U.S. Pat. No. 4,933,491. For example, the moles of acetic anhydride used in the present process are less than 6%, more typically less than about 3%, of the moles of NDA present during the purification process. Since acetic anhydride is an essential component of the present invention, the purification process normally is operated under substantially anhydrous conditions, e.g., the maximum amount of water which may be detected during operation of the process is about 1 weight percent based on the total weight of the acetic acid and acetic anhydride.

The purification process provided by the present invention may be carried out over a wide range of temperatures, pressures and times. Residence or reaction times can extend up to about 6 hours but preferably are in the range of about 5 minutes to 2 hours and more preferably from about 5 minutes to 1 hour. The process may be operated at temperatures in the range of from about 100° to 200° C., preferably from about 100 to 175° C. It should be understood that time and temperature are related such that high reaction temperatures require shorter reaction times. Pressure is not an important element of the present invention except to the extent that elevated pressures, e.g., total pressures up to about 8 bar absolute, are required to maintain the purification/reaction slurry/mixture in a liquid state.

The NDA which may be purified according to the process of this invention may be any isomer or mixture of isomers of naphthalenedicarboxylic acid.

However, the NDA preferably comprises primarily 2,6-naphthalenedicarboxylic acid, i.e., 2,6-NDA containing less than about 5 mole percent of other NDA isomers.

When the purification/reaction period is complete, the purified, solid NDA is collected by conventional liquid/solid separation techniques, e.g., filtration or centrifugation, and washed with a small amount of acetic acid to give an NDA with a greatly reduced metal content. The separation of the NDA may be done at ambient temperature but preferably is carried out at an elevated temperature, e.g., at least 40° C., preferably in the range of about 80° to 150° C.

EXAMPLES

The process provided by our invention and its operation is further illustrated by the following non-limiting examples.

Unless specified otherwise, the examples were carried out using an apparatus comprising a 3-neck, round-bottom flask equipped with a mechanical stirrer, reflux condenser, heating mantle, thermowell, and filter funnel having a coarse frit. Samples of the crude oxidation product and purified material were analyzed for NDA and TMA using standard techniques involving the formation of a trimethyl silyl derivative followed by gas chromatography. The concentrations of heavy metals (Co and Mn) in the crude and purified were determined by x-ray fluoresence spectroscopy. Unless specified otherwise, all percentage and ppm values are by weight.

Examples 1

A 300 mL flask was charged with 50 g of crude 2,6-NDA that contained 1600 ppm cobalt and 3800 ppm Mn residual catalyst metals and 2.3% TMA. Acetic acid (75 g) was added to the flask followed by the addition of 2 g acetic anhydride. The resulting mixture was heated with stirring at reflux (118° C.) for 1 hour. The mixture was cooled to 40° C. and filtered to collect the 2,6-NDA. The residue was washed with 50 mL of acetic acid and dried. The dry 2,6-NDA was found to contain 92 ppm Co, 338 ppm Mn and 0.48% TMA. This example shows that the addition of acetic anhydride solublizes the catalyst metals and trimelletic acid complexes, allowing the solid 2,6-NDA to be separated at higher purity.

Example 2

The procedure of Example 1 was repeated except that 1 g of acetic anhydride was used. The dry NDA contained 559 ppm Co, 1400 ppm Mn and 0.89% TMA.

Comparative Example

The procedure of Example 1 was repeated except that no acetic anhydride was used. The dry NDA contained 1400 ppm Co, 3500 ppm Mn and 1.97% TMA.

Example 3

A 300 mL flask was charged with acetic acid (104 g) and 26 g of crude NDA that contained 443 ppm cobalt and 5700 ppm Mn residual catalyst metals and 5.6% TMA. The resulting mixture was heated to reflux (118° C.) and acetic anhydride (1.5 g) was added. The mixture was heated at reflux for 6 minutes and rapidly cooled to 80° C. and filtered to collect the NDA. The residue was washed with 100 mL of acetic acid and dried. The dry NDA (24.5 g) was found to contain 249 ppm Co, 3300 ppm Mn, and 1.5% TMA.

Example 4

The procedure described in Example 3 was repeated except the mixture was heated at reflux for 30 minutes after the addition of acetic anhydride. The resulting dry NDA contained 115 ppm Co, 1400 ppm Mn and 0.92% TMA.

Examples 5

A 1 liter titanium autoclave equipped with a metering pump was charged with 200 g of acetic acid and 50 g of crude NDA that contained 443 ppm cobalt and 5700 ppm Mn residual catalyst metals and 5.6% TMA. The mixture was heated to 150° C. and 2.7 g of acetic anhydride was added to the mixture by means of the metering pump over a two minute time period. The resulting mixture was heated at 150° C. for 30 minutes and then quickly cooled to 80° C. in less than 15 minutes. The product mixture was filtered at 80° C. to collect the purified NDA. The NDA was washed with 100 mL of acetic acid and dried. The dry purified 2,6-NDA (43.4 g) contained 45 ppm Co, 332 ppm Mn, and 1.1% TMA. Treatment at 150° C. produces similar results to those obtained at reflux but in half the time.

Reference Example

A 100 mL flask equipped with a magnetic spin bar and heating mantle was charged with the cobalt/trimellitic acid complex having the formula $Co(TMA)_2(H_2O)_2$ (2.0 g; 4 millimole) and acetic acid (20 g). The resulting slurry was heated to boiling (118° C.) and acetic anhydride (1.62 g; 16 millimole) was added. The mixture was boiled for one minute during which time the cobalt complex dissolved to give a deep blue solution. The mixture was allowed to cool and was analyzed by liquid chromatography. Analysis showed all trimellitic acid had been converted to trimellitic anhydride. The mixture remained homogeneous after cooling. This example clearly shows that the acetic anhydride decomposes the undesirable complex allowing recovery of the expensive cobalt catalyst metals is solution. If necessary or desired, the organics can be readily extracted from the metals using countercurrent extraction methods known in the art. The Co can then be returned to the oxidizer.

The invention has been described in detail with particular reference to preferred embodiments thereof, but it will be understood that variations and modifications can be effected within the spirit and scope of the invention.

We claim:

1. Process for the removal of impurities comprising heavy metal catalyst residues and trimellitic acid (TMA) from naphthalenedicarboxylic acid (NDA) which comprises contacting a mixture comprising a slurry of finely divided NDA containing such impurities in acetic acid with acetic anhydride, wherein the metal impurities are present as complexes with trimellitic acid and the amount of acetic anhydride employed gives an acetic anhydride:TMA mole ratio of about 1:1 to 5:1.

2. Process according to claim 1 wherein the process is carried out at a temperature of about 100° to 200° C. and the heavy metal catalyst residues comprise cobalt and manganese.

3. Process for the removal of impurities comprising cobalt, manganese and trimellitic acid (TMA) from 2,6-naphthalenedicarboxylic acid (2,6-NDA) which comprises contacting at a temperature of about 100° to 200° C. a mixture comprising a slurry of finely divided 2,6-NDA containing such impurities in acetic acid with acetic anhydride, wherein the metal impurities are present as complexes with trimellitic acid, the weight ratio of acetic acid to 2,6-NDA is about 1:1 to 3:1, and acetic anhydride is used in an amount which gives an acetic anhydride:TMA mole ratio of about 1:1 to 5:1.

4. Process according to claim 3 wherein the the process is carried out at a temperature of about 100° to 175° C.

* * * * *